(12) United States Patent
Beck et al.

(10) Patent No.: US 11,478,197 B2
(45) Date of Patent: Oct. 25, 2022

(54) MEDICAL IMAGING APPARATUS AND SENSOR ARRANGEMENT THEREFOR FOR ACQUIRING AT LEAST ONE ITEM OF PATIENT MOVEMENT INFORMATION DURING A MEDICAL IMAGING EXAMINATION

(71) Applicant: Siemens Healthcare GmbH, Erlangen (DE)

(72) Inventors: Thomas Beck, Erlangen (DE); Daniel Nico Splitthoff, Uttenreuth (DE); Steffen Schroeter, Fuerth (DE)

(73) Assignee: Siemens Healthcare GmbH, Erlangen (DE)

( * ) Notice: Subject to any disclaimer, the term of this patent is extended or adjusted under 35 U.S.C. 154(b) by 540 days.

(21) Appl. No.: 16/142,695

(22) Filed: Sep. 26, 2018

(65) Prior Publication Data
US 2019/0090819 A1 Mar. 28, 2019

(30) Foreign Application Priority Data
Sep. 26, 2017 (DE) .......................... 102017217101.4

(51) Int. Cl.
*A61B 6/04* (2006.01)
*A61B 5/00* (2006.01)
*A61B 5/055* (2006.01)

(52) U.S. Cl.
CPC ............ *A61B 5/721* (2013.01); *A61B 5/0077* (2013.01); *A61B 5/055* (2013.01); *A61B 5/702* (2013.01); *A61B 6/04* (2013.01)

(58) Field of Classification Search
CPC .......... A61B 5/721; A61B 5/702; A61B 6/04; A61B 5/0077; A61B 5/0555
See application file for complete search history.

(56) References Cited

U.S. PATENT DOCUMENTS

| | | | |
|---|---|---|---|
| 2007/0019787 A1* | 1/2007 | Zuckier | G01N 23/04 378/63 |
| 2007/0066887 A1* | 3/2007 | Mire | A61B 90/39 600/424 |
| 2008/0297150 A1 | 12/2008 | Fath et al. | |
| 2015/0077113 A1 | 3/2015 | Benner | |
| 2015/0359464 A1 | 12/2015 | Olesen et al. | |
| 2016/0228005 A1 | 8/2016 | Bammer et al. | |

(Continued)

OTHER PUBLICATIONS

Zaitsev, et al. "Magnetic resonance imaging of freely moving objects: Prospective real-time motion correction using an external optical motion tracking system" NeuroImage, vol. 31, pp. 1038-1050, (2006).

(Continued)

*Primary Examiner* — Bill Thomson
*Assistant Examiner* — Delia M. Appiah Mensah
(74) *Attorney, Agent, or Firm* — Banner & Witcoff Ltd.

(57) ABSTRACT

A medical imaging apparatus, and a sensor arrangement for acquiring at least one item of patient movement information during a medical imaging examination, have at least one sensor element and a support apparatus, with the at least one sensor element arranged on the support apparatus. The support apparatus has a positioning element for positioning the support apparatus and at least one strut-like support element on which the at least one sensor element is removably arranged.

25 Claims, 3 Drawing Sheets

(56) References Cited

U.S. PATENT DOCUMENTS

2017/0143271 A1    5/2017  Gustafsson et al.
2018/0078225 A1*   3/2018  Spencer ............... A61B 5/0077
2018/0199999 A1*   7/2018  Syverson ............... A61B 90/00
2018/0207794 A1*   7/2018  Sebring ..................... B25J 5/04

OTHER PUBLICATIONS

Splitthoff, et al. "Procedure for Using Mirrors while Maintaining a Line of Sight for Cameras of Motion Correction Systems in Magnetic Resonance Imaging" Siemens AG File 989C281 (2017).

* cited by examiner

MEDICAL IMAGING APPARATUS AND SENSOR ARRANGEMENT THEREFOR FOR ACQUIRING AT LEAST ONE ITEM OF PATIENT MOVEMENT INFORMATION DURING A MEDICAL IMAGING EXAMINATION

BACKGROUND OF THE INVENTION

Field of the Invention

The present invention concerns a sensor arrangement for acquiring at least one item of patient movement information during a medical imaging examination. The present invention further concerns a medical imaging apparatus having a patient receiving zone, a housing wall surrounding the patient receiving zone, and such a sensor arrangement.

Description of the Prior Art

In medical imaging examinations that require an extended measurement time, such as magnetic resonance examinations, SPECT examinations, PET examinations etc., patient movement can result in artifacts in the medical cross-sectional images. Correcting such patient movement in the acquired medical image data can at least reduce these artifacts. However, maximally accurate patient movement information during the medical imaging examination is required for correcting such patient movements in the acquired medical image data.

Patient movement data during the medical imaging examination have conventionally been acquired using movement detectors that are preferably arranged within a patient receiving zone of the medical imaging apparatus. These movement detectors are usually removably arranged so that, in the case of medical imaging examinations with a large space requirement, it is possible to eliminate any hindrance to the patient by removing the movement detectors. If measurements have to be repeated or measurements reproduced with identical settings and/or parameters, the removable aspect of the movement detector within the patient receiving zone makes it difficult to re-establish the original fastening position of the movement detector.

DE 10 2013 218 432 A1 describes a medical imaging apparatus including a movement detector that is arranged within a patient receiving zone.

SUMMARY OF THE INVENTION

An object of the present invention is to provide a sensor arrangement designed to acquire at least one item of patient movement information during a medical imaging examination and that is reproducibly positionable within a patient receiving zone of a medical imaging apparatus.

The above object is achieved according to the invention by a sensor arrangement for acquiring at least one item of patient movement information during a medical imaging examination, in particular a magnetic resonance examination, wherein the sensor arrangement has at least one sensor element and a support apparatus and the at least one sensor element is arranged on the support apparatus.

The support apparatus has a positioning element for positioning the support apparatus and at least one strut-like support element on which the at least one sensor element is removably arranged.

The sensor arrangement is designed to acquire movement information of a region of a patient to be examined. For example, in the case of an examination of a patient's head by the medical imaging apparatus, movement of the head and/or movement of individual parts of the head, such as an eye movement, can advantageously be detected by the sensor arrangement. Movement correction can be implemented in the acquired medical image data on the basis of the movement information, by a computer.

The sensor arrangement has at least one sensor element. The at least one sensor element preferably is a camera designed to acquire patient movement information during the medical imaging examination. In addition to the at least one sensor element, the sensor arrangement can also have at least one further sensor element or further sensor elements. The at least one further sensor element and/or the further sensor elements can be of the same type as the initially described at least one sensor element, such as two or more cameras of the same construction, which are designed for acquiring patient movement information during the medical imaging examination. Alternatively, the at least one further sensor element and/or the further sensor elements can be of different construction from the initially described at least one sensor element.

As noted, the sensor arrangement has a support apparatus with a strut-like support element on which the at least one sensor element is arranged (mounted or attached). The strut-like support element is designed such that the at least one sensor element can be introduced into the patient receiving zone by the strut-like support element. The support apparatus is designed such that an identical position for the at least one sensor element is always achieved upon introduction of the support apparatus into the patient receiving zone. For example, the at least one strut-like support element for this purpose has a predetermined or defined length that establishes or determines or defines the position of the at least one sensor element. Due to the removable arrangement of the at least one sensor element, the latter can be arranged within the patient receiving zone separately from the support apparatus. A particularly space-saving arrangement can be provided in this manner.

The positioning element can have a limit stop element that establishes a position of the strut-like support element with regard to the medical imaging apparatus, in particular within the patient receiving zone. The positioning element together with the strut-like support element establishes the defined position for the at least one sensor element within the patient receiving zone.

During a medical imaging examination, or for acquiring patient movement information, the at least one sensor element is located within the patient receiving zone of the medical imaging apparatus and thus close to the patient. The patient receiving zone of the medical imaging apparatus preferably has a hollow cylindrical shape and is cylindrically surrounded by a detector unit or an acquisition unit for acquiring medical image data of the medical imaging apparatus. In an embodiment wherein the medical imaging apparatus is a magnetic resonance apparatus, the detector unit or the acquisition unit is a unit called an MR scanner, that has a superconducting basic field magnet, a gradient coil arrangement and a radio-frequency (RF) antenna that cylindrically surround the patient receiving zone. In an embodiment of the medical imaging apparatus as a computed tomography apparatus, the detector unit or the acquisition unit is an X-ray detector that cylindrically surrounds the patient receiving zone.

The invention advantageously makes it possible to achieve reproducibility of the arrangement of sensor elements for acquiring patient movement information for medical imaging examinations. This also makes it possible to verify measurements and/or to reduce measurement inaccuracies due to different arrangements of the sensor elements. In particular, in the event of repetition of a measurement, the at least one sensor element can be arranged at and/or introduced into the same position within the patient receiving zone by the support apparatus. Due to the arrangement of the at least one sensor element or a number of sensor elements within the patient receiving zone during the medical imaging examination, it is possible for the at least one sensor element or the multiple sensor elements to be brought advantageously close to the patient, such that particularly precise and accurate detection of patient movement during the medical imaging examination can be achieved. In addition, the present invention enables simple and rapid cleaning of the sensor arrangement and the patient receiving zone, since the sensor arrangement can be removed from the patient receiving zone for such cleaning.

In an embodiment of the invention, the sensor arrangement has at least one further sensor element. This enables a preferred acquisition of patient movement information during the medical imaging examination from different viewing angles or acquisition angles of the individual sensor elements relative to the patient, in particular relative to the region to be examined of the patient.

In a further embodiment, the support apparatus has at least one support element, wherein the at least one support element is adjustable in length. This enables an advantageous adaptation of the sensor unit to different medical imaging apparatuses, in particular to different lengths of patient receiving zones of different medical imaging apparatuses. In addition, a simple sensor arrangement can be provided, by which different medical imaging apparatuses can subsequently be retrofitted with sensor elements for acquiring patient movement information during the medical imaging examination. An adjustable length of the at least one support element means that the length can be reproducibly adjusted and/or reproducibly adapted by a user, in particular a medical operator (technician). The at least one support element, for example, can have a rail extension, such that particularly simple, reproducible adaptation of the length of the at least one support element can be achieved.

In a further embodiment of the invention, the at least one support element has a positioning element. With the at least one positioning element, it is possible to provide simple and rapid adaptation of the sensor arrangement, in particular of the support apparatus, to different medical imaging apparatuses. The at least one positioning element can have a positioning mark on the at least one support element. The positioning mark can be used for positioning the at least one sensor element. Alternatively or additionally, the at least one positioning element can be provided for adjusting a length of the at least one supporting element. The at least one positioning element can be a latch element that has a latching position on the support element for a defined length of the at least one support element. Further embodiments of the positioning elements are conceivable. Preferably, the support apparatus has at least one support element with at least two positioning elements in order also to take account of different embodiments of patient receiving zones in different medical imaging apparatuses.

The support apparatus can have a travel unit. The travel unit preferably has a number of rolling bodies or rolling elements, such as wheels, by which the sensor arrangement is made mobile. The sensor arrangement in this manner can be advanced into the patient receiving zone as required, in particular in the event of medical imaging examinations which require the acquisition of patient movement information. In addition, the sensor arrangement can be particularly simply removed (extracted) from the patient receiving zone in the event of a medical imaging examination with an elevated space requirement. This additionally enables simple use, i.e. arrangement, of the sensor arrangement within the patient receiving zone only as required for a user.

In a further embodiment, the sensor arrangement has an arcuate frame on which the at least one sensor element is arranged. A further sensor element and/or further sensor elements are advantageously also arranged on the arcuate frame in addition to the sensor element. An advantage of such an embodiment is that the sensor element, in particular the arcuate frame, can be arranged compactly within the patient receiving zone. In particular, spacings between the individual sensor elements can be maintained in this manner, even if the frame is removed from the patient receiving zone. The arcuate shape of the frame is preferably adapted to a cylindrical housing wall that surrounds the patient receiving zone, such that the sensor arrangement can be arranged within the patient receiving zone at a small distance from the housing wall. In addition, it is possible to avoid any significant restriction of the space available to a patient during the medical imaging examination. The arcuate frame preferably has a circular arc-shaped frame, the outer radius of which at most corresponds to an internal radius of the housing wall.

The invention further concerns a medical imaging apparatus including a patient receiving zone, a housing wall surrounding the patient receiving zone and a sensor arrangement designed to acquire at least one item of patient movement information during a medical imaging examination, in particular a magnetic resonance examination, wherein the sensor arrangement has at least one sensor element and a support apparatus. The support apparatus has a positioning element for positioning the support apparatus and at least one strut-like support element on which the at least one sensor element is removably arranged.

The invention makes it possible to achieve reproducibility of an arrangement of sensor elements for acquiring patient movement information for medical imaging examinations. This also makes it possible to verify measurements and/or to reduce measurement inaccuracies due to different arrangements of the sensor elements. In particular, in the event of repetition of a measurement, the at least one sensor element can be arranged at and/or introduced into the same position within the patient receiving zone by means of the support apparatus. Due to the arrangement of the at least one sensor element or multiple sensor elements within the patient receiving zone during the medical imaging examination, it is possible for the at least one sensor element or indeed the multiple sensor elements to be brought advantageously close to the patient, such that particularly precise and accurate detection of patient movement during the medical imaging examination is achieved. In addition, the apparatus of the invention enables simple and rapid cleaning of the sensor arrangement and of the patient receiving zone, since the sensor arrangement can be removed from the patient receiving zone for cleaning.

The advantages of the medical imaging apparatus according to the invention substantially correspond to the advantages of the sensor arrangement according to the invention, which have been explained above in detail. Features, advantages and alternative embodiments mentioned in connection with the method are also applicable to the apparatus.

The medical imaging apparatus can take the form of any medical imaging apparatuses that appears appropriate to those skilled in the art, such as a magnetic resonance apparatus, a computed tomography apparatus, a PET apparatus (positron emission tomography apparatus) etc. Particularly advantageously, however, the medical imaging apparatus is a magnetic resonance apparatus, since it is here due to the comparatively long measurement times and a sensation of claustrophobia frequently experienced by patients during a magnetic resonance examination that the present invention can be particularly advantageous. In particular, image data can also be acquired from nervous patients who make unwanted movements, and this image data can then be corrected on the basis of the movement information, such that high quality image data are available for a diagnostic finding, and repetition of the magnetic resonance examination can be avoided.

In a further embodiment of the invention, at least one sensor element can be introduced within the patient receiving zone by the support apparatus, and during a medical imaging examination the support apparatus is arranged outside the patient receiving zone. This enables simple and in particular space-saving positioning of at least one sensor element within the patient receiving zone.

The at least one sensor element, and optionally further sensor elements, are arranged within the patient receiving zone, in particular on the housing wall surrounding the patient receiving zone. The support apparatus is arranged within the patient receiving zone only during introduction of the at least one sensor element. In addition, the sensor element can be arranged within the patient receiving zone only in the case of medical imaging examinations in which patient monitoring is necessary and/or in which space required for the sensor element is still present. In this manner, pre-existing medical imaging apparatus can be particularly simply retrofitted by such a sensor arrangement.

In a further embodiment of the invention, the sensor arrangement has a frame on which at least one sensor element of the sensor unit is arranged and that can be arranged within the patient receiving zone. In particular, the frame is removably arranged on the housing wall surrounding the patient receiving zone. The frame is preferably fastenable directly to the housing wall, in particular reproducibly fastenable to the housing wall at a defined or specific position. This embodiment of the invention has the advantage that a space-saving arrangement and fastening of the frame, and thus of the at least one sensor element, can be achieved, so hindrance to the patient due to the sensor arrangement does not occur. In addition, a number of sensor elements can be arranged on the frame, such that the position of the sensor elements relative to one another is maintained due to the arrangement of the frame within the patient receiving zone. In this manner, only the frame needs to be positioned within the patient receiving zone in order to position the sensor elements. The frame can advantageously be arranged on the housing wall surrounding the patient receiving zone.

In a further embodiment, the sensor arrangement has at least one positioning element that is arranged on the housing wall surrounding the patient receiving zone. The positioning element advantageously makes it possible to establish a position of the frame, and thus the at least one sensor element, in order to arrange the at least one sensor element so that a reproducible arrangement of the at least one sensor element and the frame is achieved. To this end, the at least one positioning element is also preferably arranged within the patient receiving zone while the at least one sensor element and/or frame is being removed, such that the position of the at least one sensor element and/or frame within the patient receiving zone is still marked. The positioning element is preferably arranged directly on the housing wall surrounding the patient receiving zone. The sensor unit preferably has at least two positioning elements spaced from one another, which are arranged on the housing wall surrounding the patient receiving zone, wherein the at least one sensor element and/or the frame is arranged between the two positioning elements. The position of the frame and the at least one sensor element within the patient receiving zone thus can advantageously be accurately and durably established by the at least two positioning elements. Preferably, a first positioning element is arranged at a first end of a positioning range for the frame or the at least one sensor element arranged on the housing wall, and a second positioning element is arranged at a second end of the positioning range for the frame or the at least one sensor element arranged on the housing wall.

In another embodiment, the at least one positioning element has an L-shape, which achieves a simple positioning of the frame and/or of the at least one sensor element within the patient receiving zone. It is possible in this manner to predetermine or establish the position of the frame and the at least one sensor element in two spatial directions by the use of the L-shaped positioning element. An internal angle of the L-shaped positioning element preferably corresponds to an external angle of the frame, or of the at least one sensor element, such that the positioning element provides a unique position for the frame or the at least one sensor element on the housing wall surrounding the patient receiving zone.

In another embodiment of the invention, the frame or the at least one sensor element can be arranged in an interlocking or force-locking manner on the housing wall surrounding the patient receiving zone. As used herein, "force-locking" means components that are held together by virtue of one component being inserted into the other component, with the friction between the respective surfaces of those components serving to normally hold those components together. The components can be separated, however, by applying a force that exceeds the friction. This achieves the advantage that the frame and/or the at least one sensor element can be reproducibly arranged on the housing wall surrounding the patient receiving zone. The frame or the at least one sensor element can advantageously be arranged directly on the housing wall surrounding the patient receiving zone by a hook and loop fastener, or by other fastening elements that appear reasonable to those skilled in the art.

The medical imaging apparatus can have a patient bed with a support surface on which an examination subject is placed, with the at least one positioning element arranged on the housing wall opposite the support surface. This achieves a particularly advantageous arrangement of the sensor element of the sensor arrangement, for monitoring patient movement of a subzone of the patient to be examined during a medical imaging examination.

DESCRIPTION OF THE PREFERRED EMBODIMENTS

Figure 1:
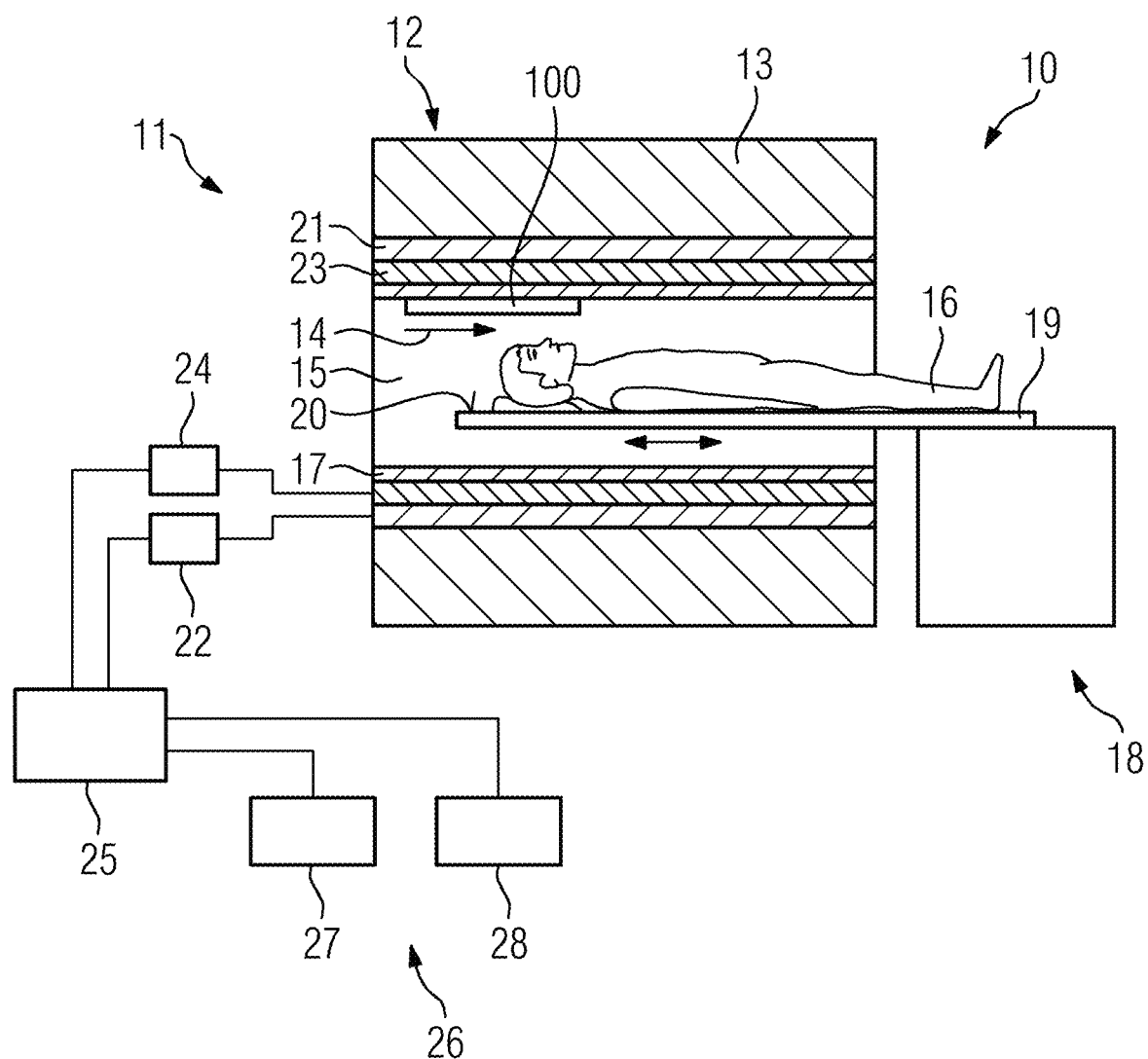
FIG. 1 schematically illustrates a medical imaging apparatus according to the invention, which includes a sensor arrangement according to the invention.

FIG. 1 schematically shows a medical imaging apparatus. In the exemplary embodiment, the medical imaging apparatus is a magnetic resonance apparatus 11, so the present invention is explained on the basis of the example of a magnetic resonance apparatus 11. The present invention is, however, not limited to the embodiment of the medical imaging apparatus as a magnetic resonance apparatus 11, and further embodiments of the medical imaging apparatus are conceivable, such as a computed tomography apparatus, etc.

The magnetic resonance apparatus 11 has a scanner 12 with a superconducting basic field magnet 13 that generates a strong and constant basic magnetic field 14. The scanner 12 has a patient receiving zone 15 for receiving a patient 16. In the exemplary embodiment, the patient receiving zone 15 is cylindrical in shape and is circumferentially surrounded by the scanner 12. The patient receiving zone 15 in this embodiment is cylindrically surrounded by a housing wall 17 of the scanner 12. In principle, however, the patient receiving zone 15 can be shaped in a different manner.

The patient 16 can be moved into the patient receiving zone 15 by a patient positioning device 18 of the magnetic resonance apparatus 11. The patient positioning device 18 has a patient bed 19 with a support surface 20, which is configured to be mobile within the patient receiving zone 15.

The scanner 12 furthermore has a gradient coil arrangement 21 for generating magnetic field gradients, which are used for spatial encoding of the MR signals during imaging. The gradient coil arrangement 21 is controlled by a gradient controller 22 of the magnetic resonance apparatus 11. The scanner 12 furthermore has a radio-frequency antenna 23 controlled by a radio-frequency antenna controller 24 so as to radiate radio-frequency pulse sequences into an examination volume, which is substantially formed by the patient receiving zone 15 of the scanner 12. The radiated radio-frequency pulse sequences excite certain nuclear spins in the patient 16, so as to cause the excited nuclear spins to emit RF signals (MR signals), which are detected by the same antenna from which the RF pulses were radiated, or by a different antenna. The acquired MR signals can be reconstructed into image data, which can be displayed so as to depict the region of the patient 16 from which the MR signals were acquired.

The magnetic resonance apparatus 11 has a system control computer 25 that controls the basic field magnet 13 and the gradient controller 22 and the radio-frequency antenna controller 24. The system control computer 25 provides central control of the magnetic resonance apparatus 11, such as for the performance of a predetermined imaging gradient echo sequence. In addition, the system control computer 25 has an evaluation processor (not shown) that evaluates medical image data acquired during the magnetic resonance examination.

The magnetic resonance apparatus 11 furthermore has a user interface 26 connected to the system control computer 25. Control information such as imaging parameters, and reconstructed magnetic resonance images, can be displayed on a display unit 27, for example on at least one monitor, of the user interface 26 for a medical operator. The user interface 26 furthermore has an input unit 28, via which information and parameters can be entered by the medical operator during a measurement procedure.

In order to acquire movement data of the patient 16 during the medical imaging examination, the present invention has a sensor arrangement 100 that is removably arranged within the patient receiving zone 15 of the scanner 12. The sensor arrangement 100 is designed such that an arrangement of the sensor arrangement 100 within the patient receiving zone 15 of the medical imaging apparatus 10 can be reproduced in a simple manner for further medical imaging examinations. The sensor arrangement 100 is preferably arranged within the patient receiving zone 15 on a region opposite the lying surface 20 of the patient bed 19.

Figure 2:
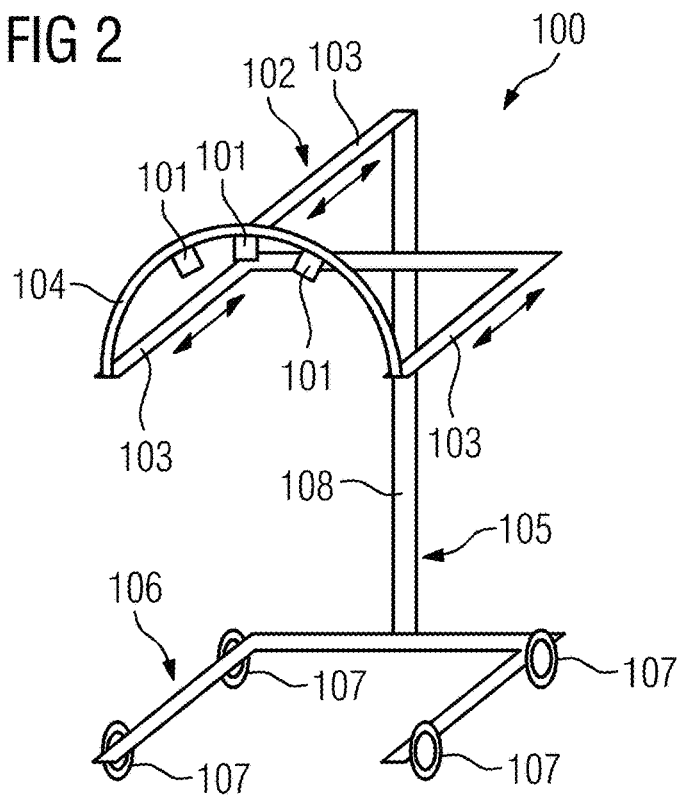
FIG. 2 is a perspective front view of the sensor arrangement according to the invention.
Figure 3:
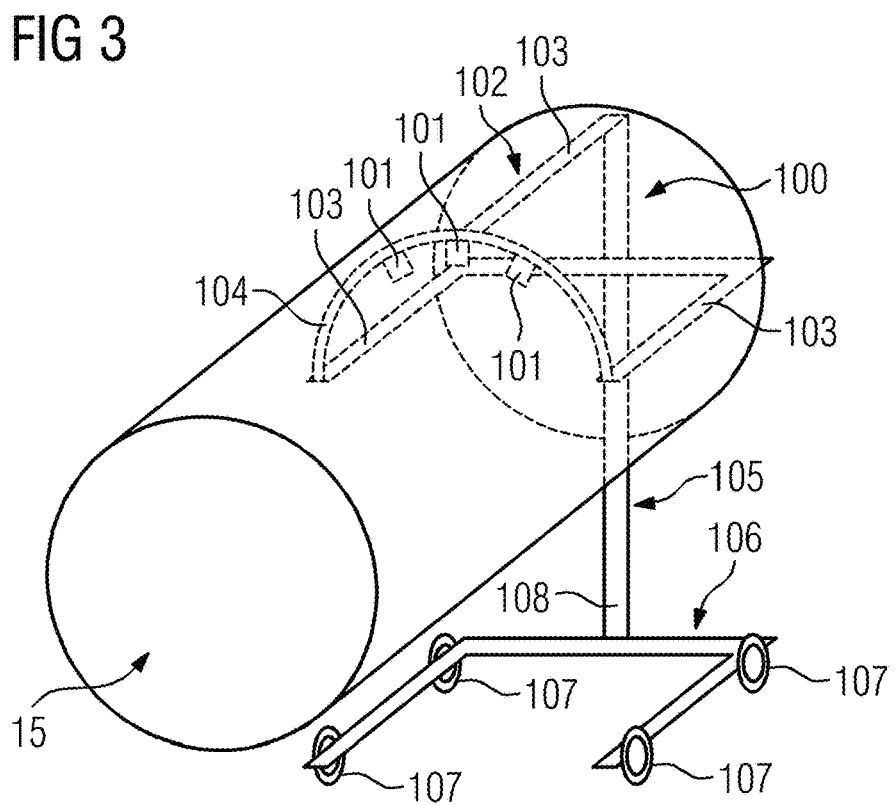
FIG. 3 is a perspective front view of the sensor arrangement within a patient receiving zone of the medical imaging apparatus.
Figure 4:
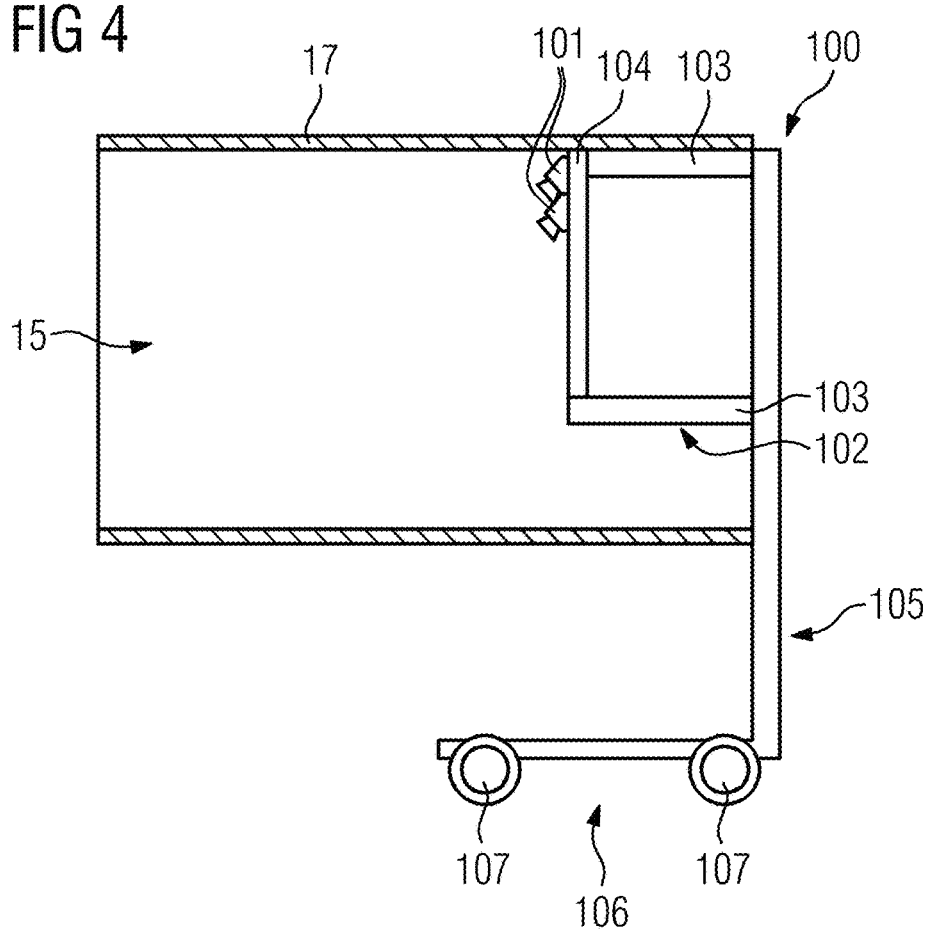
FIG. 4 is a side view of the sensor arrangement which is arranged within the patient receiving zone of the medical imaging apparatus.

As can be seen in FIG. 2 to FIG. 4, the sensor arrangement 100 has for this purpose at least one sensor element 101. In the exemplary embodiment, the sensor arrangement 100 has three sensor elements 101. In an alternative embodiment of the invention, the sensor arrangement 100 can also have more than three sensor elements 101 or indeed just one single sensor element 101 or two sensor elements 101. The individual sensor elements 101 are designed for acquiring patient 16 movement information during the medical imaging examination, in particular the magnetic resonance examination. In the present case, the individual sensor elements 101 are each a camera, and the individual sensor elements 101 can be cameras of like construction for acquiring the at least one item of patient 16 movement information.

The sensor arrangement 100 furthermore has a support apparatus 102 on which the three sensor elements 101 are arranged. The support apparatus 102 is designed to introduce the sensor elements 101 for acquiring the patient 16 movement information for a medical imaging examination of the patient receiving zone 15. During the medical imaging examination, only the sensor elements 101 are arranged within the patient receiving zone 15, while the support apparatus 102 is outside the patient receiving zone 15. In this manner, the sensor elements 101, in particular the three sensor elements 101, are arranged within the patient receiving zone 15 during acquisition of the patient 16 movement information and thus close to the patient 16 and/or at a short distance from the patient 16 within the patient receiving zone 15.

By the use of the support apparatus 102, it is also possible to arrange the sensor elements 101 within the patient receiving zone 15 only for those medical imaging examinations in which acquisition of patient 16 movement information is desirable. For medical imaging examinations in which acquisition of patient 16 movement information is not necessary, or for cleaning of the medical imaging apparatus 10 and the sensor arrangement 100, the sensor arrangement 100 can thus be removed from the patient receiving zone 15, such that more space is available for the patient 16 during the medical imaging examination.

In the exemplary embodiment, the support apparatus 102 has at least one strut-like support element 103 and a positioning element 108. The sensor arrangement 100 additionally has a frame 104 which is arranged on the at least one strut-like support element 103 and on which the sensor elements 101 are also arranged. The frame 104 of the sensor arrangement 100, on which the sensor elements 101 are arranged, is of arcuate, in particular circular arc-shaped, construction. An arcuate shape of the frame 104 is preferably adapted to the cylindrical housing wall 17 which surrounds the patient receiving zone 15, such that the sensor arrangement 100, in particular the sensor elements 101, can be arranged within the patient receiving zone 15 at a small distance from the housing wall 17. Due to the arcuate shape of the frame 104, the sensor elements 101 can be arranged particularly close to the housing wall 17 surrounding the patient receiving zone 15 of the medical imaging apparatus 10, in particular of the magnetic resonance apparatus 11.

In the present exemplary embodiment, the positioning element 108 of the support apparatus 102 takes the form of a limit stop element which, on introduction of the support unit 102 into the patient receiving zone 15, comes to a limit stop on the housing of the magnet unit 12. Further embodiments of the positioning element that may appear reasonable to those skilled in the art are also conceivable.

For simple and reproducible arrangement of the individual sensor elements 10 on the arcuate frame 104, the frame 104 can also have positioning elements, wherein the positioning elements are not shown in greater detail in FIGS. 2 to 5. In the present exemplary embodiment, the arcuate frame 104 has three positioning elements, such that an accurate position for each sensor element 101 is marked on the arcuate frame 104. The individual positioning elements are arranged spaced apart from one another on the arcuate frame 104. This embodiment permits a reproducible arrangement of the individual sensor elements 101 on the support apparatus 102, in particular on the arcuate frame 104.

In the exemplary embodiment, the support apparatus 102 has a number of strut-like support elements 103, wherein the plurality of strut-like support elements 103 are adjustable with regard to the length thereof. The arcuate frame 104 for arranging the three sensor elements 101 is arranged at the end regions of each of the plurality of strut-like support elements 103. In the exemplary embodiment, the support apparatus 101 has three strut-like support elements 103, each of which is adjustable with regard to the length thereof. It can additionally also be provided that the frame 104 on which the sensor elements 101 are arranged is also adjustable with regard to the length thereof.

The individual ones of the number of strut-like support elements 103 have, for example, a rail extension for adjusting the length thereof. In addition, the number of strut-like support elements 103 of the support apparatus 102 can also each have at least one positioning element. Preferably, however, each of the strut-like support elements 103 of the support apparatus 102 has two or more positioning elements that can be, for example, latch elements. In this manner, a length setting can be accurately established and thus different lengths of the number of strut-like support elements 103 can also be simply and accurately established and set for different embodiments of patient receiving zones 15.

In the exemplary embodiment, the sensor arrangement 100 furthermore has a frame unit 105. The support apparatus 102 is arranged on the frame unit 105. The frame unit 105 additionally has a travel unit 106. The travel unit 106 preferably has a number of rolling bodies or rolling elements 107, such as wheels, by which the sensor arrangement 100 can be moved and advanced into the patient receiving zone 15. The support apparatus 102 is arranged at a first end region of the frame unit 105 and the travel unit 106 at a second end region of the frame unit 105. The first end region and second end region of the frame unit 105 have opposing end regions of the frame unit 105. The arrangement of the travel unit 106 on the frame unit 105 and the arrangement of the support apparatus 102 on the frame unit 105 are designed such that the sensor arrangement 100 is of C-shaped construction.

The support apparatus 102 is arranged on the frame unit 105 such that, upon introduction of the support apparatus 102 into the patient receiving zone 15, the support apparatus 102 is arranged on a region within the patient receiving zone 15 which is opposite the lying surface 20 of the patient bed 19. By the use of the support apparatus 102, the individual sensor elements 101 can thus be arranged at a small distance from the housing wall 17 surrounding the patient receiving zone 15. The region of the housing wall 17 surrounding the patient receiving zone 15 is arranged opposite the lying surface 20 of the patient bed 19.

The frame unit 105 can additionally be designed to be height-adjustable, such that the sensor arrangement 100 can be adapted to different heights of patient receiving zones 15 of different imaging apparatuses 10. The frame unit 105 can also have a number of frame elements that are displaceable within one another. A frame unit 105 of such a design can also have latch elements and/or fastening elements, such that easy adaptation of the height of the frame unit 105 to different medical imaging apparatuses is possible in a simple manner.

Figure 5:
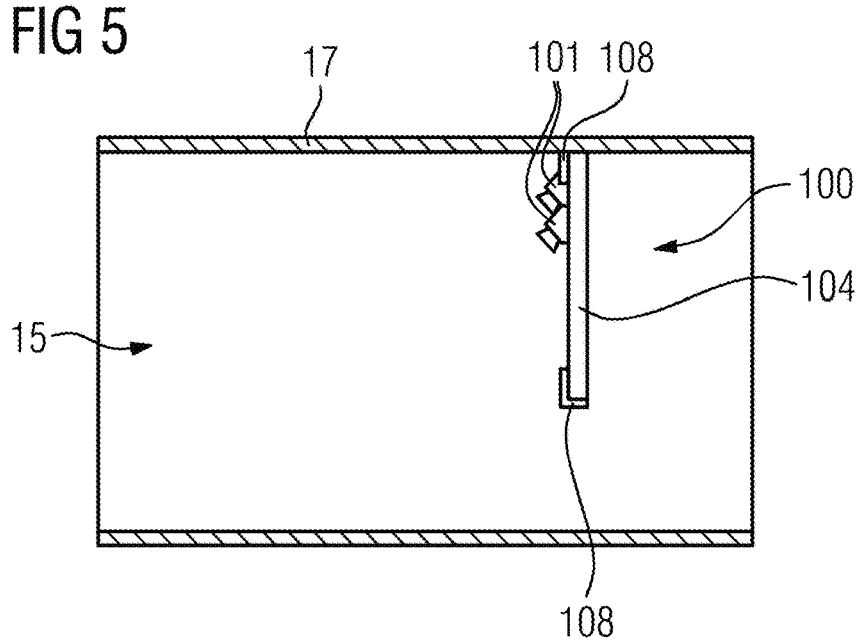
FIG. 5 is a side view of an arrangement of a frame of the sensor arrangement within the patient receiving zone of the medical imaging apparatus.

The sensor arrangement 100 furthermore has a further positioning element 108, which is arranged within the patient receiving zone 15 directly on the housing wall 17 surrounding the patient receiving zone 15 (FIG. 5). Such a positioning element 108 can be, for example, a limit stop that establishes an end position of the number of strut-like support elements 103 when these are advanced into the patient receiving zone 15. In the exemplary embodiment, the sensor arrangement 100 has two positioning elements 108 for positioning the arcuate frame 104. The individual positioning elements 108 are arranged directly on the housing wall 17 surrounding the patient receiving zone 15. The two positioning elements 108 are, for example, screwed to the housing wall 17 surrounding the patient receiving zone 15.

The two positioning elements 108 are spaced apart from one another on the housing wall 17 surrounding the patient receiving zone 15, wherein the arcuate frame 104 can be arranged between the two positioning elements 108. A region between the two positioning elements 108 precisely corresponds to the size of the arcuate frame 104, such that a unique position within the patient receiving zone 15 is provided for the arcuate frame 104 and in this manner reproducible positioning of the arcuate frame 104 during medical imaging examinations can be ensured. In addition, the positioning elements 108 can establish just one position of the individual sensor elements 101 within the patient receiving zone 15.

In order to facilitate positioning of the individual sensor elements 101 and/or of the arcuate frame 104 between the two positioning elements 108, the positioning elements 108 have an L-shape. An internal angle of the L-shaped positioning elements 108 preferably corresponds to an external angle of the sensor elements 101, which can be arranged between the two positioning elements 108, or of the frame 104 that can be arranged between the two positioning elements 108. Thus a unique position for the sensor elements 101 and/or the arcuate frame 104 within the patient receiving zone 15 is established by the two positioning elements 108.

For removable positioning on the housing wall 17 surrounding the patient receiving zone 15, the arcuate frame 104 has a fastening element designed for interlocking and/or force-locking fastening of the arcuate frame 104 to the housing wall 17 surrounding the patient receiving zone 15. In the present exemplary embodiment, the fastening element comprises a hook and loop fastener. The arcuate frame 104 can have a fastening element of a different configuration.

In another embodiment of the invention, in which the sensor elements 101 are arranged directly on the housing wall 17 of the patient receiving zone 15, the individual sensor elements 101 have fastening elements for arrangement within the patient receiving zone 15. The individual fastening elements can be formed by hook and loop fasteners.

The positioning elements 108 are arranged directly on a region of the housing wall 17 surrounding the patient receiving zone 15, this region being opposite the support surface 20 of the patient bed 19. The sensor elements 101 and/or the arcuate frame 104 are thus also arranged on the housing wall 17 of the patient receiving zone 15 that is opposite the support surface 20 of the patient bed 19.

The size of the frame 104 and thus the number of positioning elements 108 and/or also the number of arcuate frames 104 can be dependent on the number of sensor elements 101 and/or on an embodiment of the individual sensor elements 101 and/or on the configuration of the individual sensor elements 101.

If, for example, the sensor arrangement 100 has a single sensor element 101, the frame 104 can be selected as a function of the size of the sensor element 101. If the sensor arrangement 100 has a number of sensor elements 101 that are additionally arranged in a distributed manner within the patient receiving zone 15, the sensor arrangement 100 can also have a number of frames 104, which are additionally arranged in a distributed manner within the patient receiving zone 15, in particular arranged in a distributed manner on the housing wall 17 surrounding the patient receiving zone 15.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A sensor arrangement for acquiring an item of patient movement information during a medical imaging examination conducted with a medical image data acquisition scanner, said sensor arrangement comprising:
   a sensor supported on a movable support that is configured to position said sensor within a patient receiving zone of the medical image data scanner so that said sensor detects movement of a patient situated in the patient receiving zone of the medical imaging data scanner, wherein the medical imaging data scanner includes a positioning element disposed on a housing wall within the patient receiving zone; and
   said movable support comprising:
      a positioning structure that is configured to position the support within the medical image data scanner,
      a strut-like support having a first end and a second end opposite the first end, the first end being connected to the positioning structure, and
      an arcuate frame connected to the second end of the strut-like support, the sensor being removably mountable to the arcuate frame, wherein:
      the positioning element is configured to: establish an end position within the patient receiving zone of the strut-like support and position the arcuate frame and the sensor mounted thereon within the patient receiving zone;
      a fastener is configured to selectively fasten the arcuate frame within the patient receiving zone at the end position; and
      the arcuate frame and the sensor mounted thereon are configured to remain within the patient receiving zone, and the positioning structure and the strut-like support are configured to be removable from the patient receiving zone, when the arcuate frame is fastened at the end position.

2. A sensor arrangement as claimed in claim 1 comprising at least one further sensor mounted to said support that is also configured to detect said movement of said patient.

3. A sensor arrangement as claimed in claim 1 wherein said strut-like support has an adjustable length.

4. A sensor arrangement as claimed in claim 1 wherein said positioning structure is a part of said strut-like support.

5. A sensor arrangement as claimed in claim 1 wherein said support comprises one or more wheels that are configured to make said support mobile.

6. A sensor arrangement as claimed in claim 1 wherein said support comprises an arcuate frame to which said sensor is mounted.

7. A medical imaging apparatus comprising:
   a medical image data acquisition scanner comprising a housing wall that surrounds a patient receiving zone;
   a positioning element disposed on the housing wall within the patient receiving zone;
   a fastener; and
   a sensor arrangement configured for removable placement in said patient receiving zone, the sensor arrangement comprising: a sensor supported on a movable support that is configured to position said sensor within the patient receiving zone of the medical image data scanner so that said sensor detects movement of a patient situated in the patient receiving zone of the medical imaging data scanner, wherein;
   the movable support includes: a positioning structure that is configured to position the support within the medical image data scanner, a strut-like support having a first end and a second end opposite the first end, the first end being connected to the positioning structure, and an arcuate frame connected to the second end of the strut-like support, the sensor being removably mountable to the arcuate frame;
   the positioning element is configured to: establish an end position within the patient receiving zone of the strut-like support and position the arcuate frame and the sensor mounted thereon within the patient receiving zone;
   the fastener is configured to selectively fasten the arcuate frame within the patient receiving zone at the end position; and
   the arcuate frame and the sensor mounted thereon are configured to remain within the patient receiving zone, and the positioning structure and the strut-like support are configured to be removable from the patient receiving zone, when the arcuate frame is fastened at the end position.

8. A medical imaging apparatus as claimed in claim 7 wherein said medical imaging data scanner is a magnetic resonance scanner.

9. A medical imaging apparatus as claimed in claim 7 wherein said support is movable into and out of said patient receiving zone.

10. A medical imaging apparatus as claimed in claim 7 wherein said arcuate frame has a shape adapted to said housing wall, so that said arcuate frame is configured to be situated adjacent to said housing wall in said patient receiving zone.

11. A medical imaging apparatus as claimed in claim 7 wherein said positioning structure of said sensor arrangement is situated at said housing wall.

12. A medical imaging apparatus as claimed in claim 11 wherein said positioning structure has an L-shape.

13. A medical imaging apparatus as claimed in claim 11 wherein at least one of said arcuate frame and said sensor is interlocked to said housing wall.

14. A medical imaging apparatus as claimed in claim 11 wherein said medical image data scanner comprises a patient bed having a support surface adapted to receive a patient thereon, and wherein said positioning structure is situated on the housing wall opposite to said support surface.

15. A medical imaging apparatus as claimed in claim 7 comprising at least one further sensor mounted to said support that is also configured to detect said movement of said patient.

16. A medical imaging apparatus as claimed in claim 7 wherein said strut-like support has an adjustable length.

17. A medical imaging apparatus as claimed in claim 7 wherein said positioning structure is a part of said strut-like support.

18. A medical imaging apparatus as claimed in claim 7 wherein said support comprises one or more wheels that are configured to make said support mobile.

19. A medical imaging apparatus as claimed in claim 7 wherein the positioning structure includes an elongated member.

20. A medical imaging apparatus as claimed in claim 10 wherein the shape of the arcuate frame corresponds to an interior surface of the housing wall so that the arcuate frame is insertable within the patient receiving zone.

21. A medical imaging apparatus as claimed in claim 7, wherein the positioning structure is directly connected to the strut-like support.

22. A medical imaging apparatus as claimed in claim 7, wherein the first end of the strut-like support is directly connected to the positioning structure and the second end of the strut-like support is directly connected to the arcuate frame.

23. A medical imaging apparatus as claimed in claim 7, wherein an internal angle of the positioning element corresponds to an external angle of the sensor.

24. A medical imaging apparatus as claimed in claim 7, wherein an internal angle of the positioning element corresponds to an external angle of the arcuate frame.

25. A medical imaging apparatus as claimed in claim 7, wherein the arcuate frame comprises the fastener.

* * * * *